US011964060B2

(12) United States Patent
Hille et al.

(10) Patent No.: US 11,964,060 B2
(45) Date of Patent: Apr. 23, 2024

(54) NICOTINE-CONTAINING TRANSPARENT TRANSDERMAL THERAPEUTIC SYSTEM

(71) Applicant: LTS Lohmann Therapie-Systeme AG, Andernach (DE)

(72) Inventors: Thomas Hille, Neuwied (DE); Gabriel Wauer, Ahrweiler (DE); Petra Botzem, Andernach (DE); Frank Seibertz, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 333 days.

(21) Appl. No.: 16/488,506

(22) PCT Filed: Feb. 26, 2018

(86) PCT No.: PCT/DE2018/100168
§ 371 (c)(1),
(2) Date: Aug. 23, 2019

(87) PCT Pub. No.: WO2018/153413
PCT Pub. Date: Aug. 30, 2018

(65) Prior Publication Data
US 2020/0230074 A1    Jul. 23, 2020

(30) Foreign Application Priority Data
Feb. 27, 2017 (DE) ............... 10 2017 104 026.9

(51) Int. Cl.
| A61K 9/70 | (2006.01) |
| A61K 31/465 | (2006.01) |
| A61K 47/32 | (2006.01) |
| A61K 47/34 | (2017.01) |
| A61P 25/34 | (2006.01) |
| C09J 7/38 | (2018.01) |

(52) U.S. Cl.
CPC .......... *A61K 9/7084* (2013.01); *A61K 31/465* (2013.01); *A61K 47/32* (2013.01); *A61K 47/34* (2013.01); *A61P 25/34* (2018.01); *C09J 7/385* (2018.01)

(58) Field of Classification Search
CPC ...... A61K 31/465; A61K 47/32; A61K 47/34; A61K 9/7084; A61P 25/34; C09J 7/385
See application file for complete search history.

(56) References Cited

U.S. PATENT DOCUMENTS

| 4,908,213 A | 3/1990 | Govil et al. |
| 5,110,599 A | 5/1992 | Anhauser et al. |
| 6,187,322 B1 | 2/2001 | Hille et al. |
| 6,479,076 B2 | 11/2002 | Blank |
| 6,562,363 B1 | 5/2003 | Mantelle et al. |
| 6,699,498 B1 | 3/2004 | Muller |
| 9,763,929 B2 | 9/2017 | Rudolph et al. |
| 2004/0234585 A1* | 11/2004 | Gale ...................... A61K 47/34 424/449 |
| 2008/0008748 A1* | 1/2008 | Beyreuther ............. A61P 25/04 514/289 |
| 2014/0161739 A1 | 6/2014 | Street et al. |
| 2015/0190349 A1 | 7/2015 | Horstmann |
| 2016/0199316 A1* | 7/2016 | Breitenbach ........... A61K 31/27 604/289 |

FOREIGN PATENT DOCUMENTS

| DE | 60201134 T2 | 10/2005 |
| EP | 0525105 B1 | 2/1996 |
| EP | WO 2014/198423 A1 * | 12/2014 ........... A61K 31/381 |
| JP | S59196817 A | 11/1984 |
| JP | 2002539239 A | 11/2002 |
| JP | 2007262007 A | 10/2007 |
| JP | 2012214425 A | 11/2012 |
| RU | 2234337 C2 | 8/2004 |
| RU | 2263503 C1 | 11/2005 |
| RU | 2266735 C2 | 12/2005 |
| RU | 2320674 C1 | 3/2008 |
| RU | 2356553 C2 | 5/2009 |
| RU | 2501551 C2 | 12/2013 |
| RU | 2564394 C2 | 9/2015 |
| WO | 199518603 A1 | 7/1995 |

OTHER PUBLICATIONS

DyStar Industries product description for Aerotex® Resin 3730 (www.dystar.com/melamine-resins/aerotex-3730/); 2-pg PDF, downloaded Nov. 19, 2021.*
Polymer Properties Database for the prearation of Melamine-Formaldehyde Resins; (polymerdatabase.com/polymer%20classes/MelamineFormaldehyde%20type.html); 3-pg PDF downloaded Nov. 19, 2021.*
Benowitz, Neal; "Nicotine and Postoperative Management of Pain"; International Anesthesia Research Society; vol. 107, No. 3, pp. 739-741. Published Sep. 2008.*
Office Action for Japanese Application No. 2019-544928, dated Jun. 8, 2021, 3 pages.
Office Action for Canadian Application No. 3051150, dated Nov. 10, 2021, 7 pages.

* cited by examiner

*Primary Examiner* — Jeffrey T. Palenik
(74) *Attorney, Agent, or Firm* — Lippes Mathias LLP

(57) ABSTRACT

The invention relates to transparent therapeutic systems (TTS) which contain the active substance nicotine and which further contain at least one acid amide group as a lateral functional group. The TTS can be transparent and for discreet use. The invention also relates to methods for producing these TTS, said TTS being produced by methods using said polymers and being charged with active substance by way of a printing method.

20 Claims, 1 Drawing Sheet

NICOTINE-CONTAINING TRANSPARENT TRANSDERMAL THERAPEUTIC SYSTEM

Figure 1:
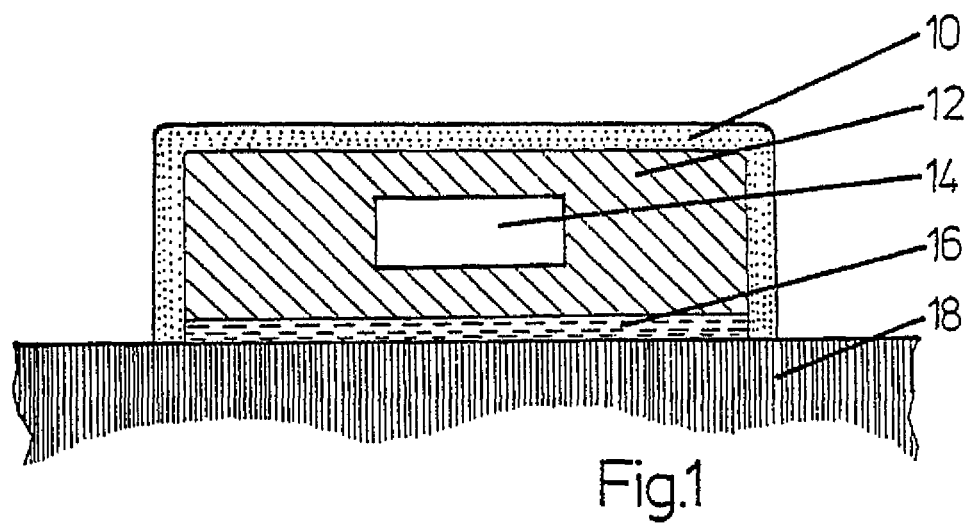

The invention relates to a transdermal therapeutic system (TTS) containing the active substance nicotine, a method for producing the TTS, and the use of a specific polymer for stabilising nicotine in the TTS.

TTS with nicotine are known in the prior art. They have already been approved and sold globally for years under the tradenames Nicotinell (Habitrol), Nicorette and Niquitin as medicinal products for combatting nicotine addiction, but are not yet in any way optimal, because either excessively large amounts of the toxic nicotine base remain in the worn TTS or the discolouration of the nicotine base leads to a TTS that is not aesthetically appealing. In this regard it should be noted that the light sensitivity of nicotine is generally known and is described for example in the Merck Index (Merck Index, 13$^{th}$ edition, 6551. Nicotine).

The application of medicinal products should take into consideration the patient's need for discretion. Thus, clearly visible, eye-catching TTS especially should be avoided. Due to the need to market TTS internationally, it would be very desirable not to use what are known as "skin-coloured" opaque films as back layers, but instead transparent, i.e. light-permeable films, in order to take into account the different skin colours of people across the world. The disadvantages of the nicotine TTS according to the prior art will now be described briefly:

The commercial product Niquitin, which is a TTS with transparent back layer, which is described in EP-A-0525105, contains 114 mg nicotine in a matrix of polyisobutylene and, according to the patient information, releases only 21 mg of active substance in 24 hours. This represents merely 18.4% of the declared content, which means that 93 mg of nicotine remain in the worn TTS and end up in household waste. This is unacceptable due to the extremely high toxicity of nicotine.

In the case of the commercial products Nicorette and Nicotinell the active substance utilisation is much better than in the case of Niquitin. Nicotinell, which releases 21 mg of nicotine, contains only 52.5 mg of nicotine, and therefore only 31.5 mg of nicotine remain unused in the TTS and 40% active substance are used therapeutically.

The situation is similar in the case of Nicorette. This TTS is worn for only 16 hours instead of 24 hours, contains 40 mg of nicotine and releases 14 mg, which corresponds to 35% and means that only 26 mg of nicotine remain unused in the TTS. Both commercial products have no transparent back layer, but instead either a beige lacquered back layer or a matt back layer.

Inadequate active substance utilisation, however, is brought about not only by the active substance that remains in the TTS, but is also caused during the production of TTS, when these are punched from web-like material, as is the case with Niquitin and Nicorette, because plaster-like medicinal products and sticking plasters with rounded corners are punched from web-like material, wherein the grid-like, active-substance-containing material between the individual plasters has to be discarded and disposed of as hazardous waste.

U.S. Pat. No. 4,908,213 discloses a TTS for administering nicotine, wherein an antipruritic active substance is additionally contained. A metallised polypropylene film is preferably used as active-substance-impermeable top layer.

JP 2007-262 007 A discloses a TTS for administering nicotine, wherein the objective is to ensure that the active substance is released continuously and constantly.

DE 602 01 134 T2 relates to a nicotine-containing gel for smoking cessation which intends to ensure a slow and delayed release of nicotine.

US 2015/0 190 349 A1 discloses a multi-layer TTS for administering nicotine which is intended to ensure that the TTS adheres in a stable manner to the skin of the patient.

The aim of the present invention is therefore especially to provide a nicotine-containing TTS with which a discolouration during storage is avoided or at least significantly reduced. In this way, it should be possible to provide transparent TTS which are not made unsightly by such discolouration. The method for producing said TTS shall remain the same, because the active substance utilisation is optimal and production-induced active substance losses can be largely or completely avoided.

This aim is addressed surprisingly by a transdermal therapeutic system (TTS) comprising nicotine and containing a polymer with an acid amide group as a lateral functional group for stabilising nicotine.

The invention therefore relates to a transdermal therapeutic system (ETS) containing the active substance nicotine as defined in claim 1. The TTS according to the invention surprisingly demonstrates a significantly slowed discolouration over time as compared to nicotine-containing TTS according to the prior art, and therefore a nicotine-containing TTS which does not discolour during the minimum shelf life of the medicinal product of 36 months can be provided.

The invention also relates to methods for producing these transdermal therapeutic systems, in which in a preferred embodiment the systems are charged with active substance by way of a printing method, wherein, by an adjustment process, in which individual dosing is performed, production losses of active-substance-containing, grid-like material, which usually are unavoidable when punching out individual plasters from grid-like material, are avoided. Here, the grid-like material relates to the surrounding leftover material which remains after the separation by cutting and/or stamping and which generally has the geometric form of a grid.

The invention will be explained in detail hereinafter.

TTS will be used as an abbreviation for "transdermal therapeutic system".

A light-permeable layer will be understood to mean a transparent (=see-through) or translucent (=partially see-through) layer. A transparent layer allows light to pass through almost unhindered, whereas a translucent layer allows the majority of the light to pass through, but in so doing the light scatters diffusely.

A surface is referred to as being matt if it achieves only a few gloss units (GU) on the gloss scale, which ranges from 100 GU for the gloss of the black glass standard to 0 GU for an absolutely matt surface. To this end, the reflectometer value of the surface can be determined by a gloss measurement using a reflectometer in 85° C. geometry. A matt surface preferably has a reflectometer value<10 gloss units (GU).

The layers of a preferred embodiment of the TTS according to the invention are clear and see-through. In a preferred embodiment the TTS according to the invention is transparent, especially transparent and colourless. In an alternative embodiment the TTS can also have a back layer with matt surface.

The transparency of a material, such as a TTS or a film or layer, can be determined by ascertaining the light transmitted through or absorbed by the material, for example by means of a Macbeth 1500/Plus color measuring system (Kollmorgen Instruments Corp., Newburgh, N.Y., USA).

The percentage of incident light that is absorbed as it passes through the material is the opacity index.

A material such as a TTS or a film or layer is considered here to be transparent if the opacity index is less than 50%. The TTS, or the TTS from which the detachment film has been removed, in a preferred embodiment has an opacity index of less than 50% and preferably less than 35%. The back layer in a preferred embodiment has an opacity index of less than 50%, more preferably less than 35%, and especially preferably less than 20%.

Unless otherwise specified, polymers that are pharmaceutically acceptable are preferred for all polymers cited hereinafter.

Transdermal therapeutic systems are systems for the controlled administration of pharmaceutical active substances via the skin. They have been used for a relatively long time for the treatment of various illnesses, physical as well as mental functional disorders, complaints and ailments. Transdermal therapeutic systems are generally layered products in the form of plasters, which comprise an active-substance-impermeable back layer, at least one active-substance-containing reservoir or matrix layer, optionally a membrane controlling the rate of active substance release, and a detachable protective layer, which is removed from the TTS prior to its use.

The invention relates to a transdermal therapeutic system (TTS) comprising
  a) a back layer impermeable to nicotine,
  b) an active-substance-containing layer, comprising nicotine as active substance, wherein the nicotine is in the form of a free base, and at least one polymer with at least one acid amide group as a lateral functional group, and
  c) a detachable protective layer.

The active-substance-containing layer comprises nicotine as active substance. The nicotine is in the form of a free base. Thus, there are no protonated forms or salt forms present. Pure nicotine at room temperature is a colourless, oily liquid, which quickly turns brown when exposed to air.

The ITS contains for example 10 to 400 mg, preferably 15 to 300 mg, especially 20 to 150 mg of nicotine.

The active-substance-containing layer also comprises at least one polymer with at least one acid amide group as a lateral functional group. The polymer is especially an organic polymer. The polymer is preferably a pharmaceutically acceptable polymer with at least one acid amide group as a lateral functional group.

The acid amide group is in the form of a lateral functional group, i.e. the acid amide group is located in a side chain of the polymer. By contrast, polyamides for example have an acid amide group in the main chain. The acid amide group, which is also referred to as an amide group, generally has the structural unit —NR—C(=O)—, wherein R can be hydrogen or an organic group, such as substituted or unsubstituted alkyl or substituted or unsubstituted aryl. The acid amide group can be a lactam group, i.e. a cyclic acid amide group. The acid amide group is preferably a lactam group. The acid amide group can also be an acid imide group, especially a cyclic acid imide group.

It is preferred that the nitrogen atom of the acid amide group, especially the nitrogen atom of the lactam group, is directly bonded to the main chain, especially a carbon atom of the main chain, of the polymer. The polymer with at least one acid amide group as a lateral functional group is therefore preferably an N-vinyl amide homopolymer or an N-vinyl amide copolymer, especially an N-vinyl lactam homopolymer or an N-vinyl lactam copolymer.

It is also possible that the acid amide group is bonded directly to the main chain, especially a carbon atom of the main chain, of the polymer via the carbonyl carbon of the acid amide group. Examples are acrylamide homopolymer or acrylamide copolymer. It is also possible that the acid amide group is not located directly on the main chain of the polymer, but in the side chain, and is bonded to the main chain via a linking group, for example an alkylene group.

The polymer with at least one acid amide group as a lateral functional group can be a homopolymer or a copolymer, i.e. formed from one or more monomers. All, or only part of the repetition units or monomer units of the polymer can have an acid amide group as a lateral functional group.

The proportion of monomers that have an acid amide group as a lateral functional group, in relation to all monomers that form the polymer, preferably lies in the range of from 30 to 100% by weight, preferably 50 to 100% by weight. The proportion of monomers that do not have an acid amide group as a lateral functional group lies accordingly in the range of from 0 to 70% by weight, preferably 0 to 50% by weight. In the case of a polymer that also contains a proportion of monomers that do not have an acid amide group as a lateral group, the weight ratio of one or more monomers that has/have an acid amide group as a lateral functional group to one or more monomers that does/do not have an acid amide group as a lateral functional group lies preferably in the range of from 80:20 to 30:70, more preferably 70:30 to 50:50. This is true especially for a vinylpyrrolidone-vinyl acetate copolymer.

The polymer can be formed from one or more monomers that has/have an acid amide group as a lateral functional group and possibly one or more monomers that does/do not have an acid amide group as a lateral functional group.

Examples of monomers that have an acid amide group as a lateral functional group are acrylamide and N-vinyl amide, especially N-vinyl lactams. Examples of N-vinyl amides and N-vinyl lactams are N-vinyl amide, N-vinyl-methyl acetamide, vinyl-ethyl acetamide, N-vinyl methyl-isobutyramide, N-vinyl-2-pyrrolidone, N-vinyl-3-pyrrolidone, N-vinyl-2-piperidone, N-vinyl caprolactam, N-vinyl-5-methyl-2-pyrrolidone, N-vinyl-3-methyl-2-pyrrolidone and N-vinyl imides, such as N-vinyl succinimide and N-vinyl phthalimide. N-vinyl-2-pyrrolidone is especially preferred.

Examples of monomers that do not have an acid amide group as a lateral functional group are vinyl acetate or N-vinylimidazole.

Examples of homopolymers that have an acid amide group as a lateral functional group are polyacrylamides and poly-N-vinyl amides, especially poly-N-vinyl lactams. Examples of poly-N-vinyl amides and poly-N-vinyl lactams are poly-N-vinyl amide, poly-N-vinyl-methyl acetamide, poly-N-vinyl-ethyl acetamide, poly-N-vinyl methyl-isobutyramide, poly-N-vinyl-2-pyrrolidone, poly-N-vinyl-3-pyrrolidone, poly-N-vinyl-2-piperidone, poly-N-vinyl caprolactam, poly-N-vinyl-5-methyl-2-pyrrolidone, poly-N-vinyl-3-methyl-2-pyrrolidone and poly-N-vinylimides, such as poly-N-vinylsuccinimide and poly-N-vinylphthalimide.

The polymer with at least one acid amide group as a lateral functional group is especially preferably a vinylpyrrolidone homopolymer or a vinylpyrrolidone copolymer, wherein the copolymer is preferably formed from vinylpyrrolidone and at least one comonomer selected from N-vinylimidazole, vinyl acetate and/or vinyl caprolactam. Unless specified otherwise, vinylpyrrolidone is preferably N-vinyl-2-pyrrolidone, as is usual in the art.

The polymer is very especially preferably a polyvinylpyrrolidone, especially poly(N-vinyl-2-pyrrolidone), or a vinylpyrrolidone-vinyl acetate copolymer which can be partially hydrolysed, especially a N-vinyl-2-pyrrolidone-vinyl acetate copolymer which can be partially hydrolysed. The partial hydrolysis refers here to the partial hydrolysis of the acetate group. Polyvinylpyrrolidone is also referred to as PVP or povidine and is commercially available for example under the tradename Kollidon from BASF. The polymer with at least one acid amide group as a lateral functional group, especially polyvinylpyrrolidone, is preferably soluble in water. The polyvinylpyrrolidone is especially an un-crosslinked polyvinyl pyrrolidone. Crosslinked polyvinyl pyrrolidones, which are also referred to as crospovidone, are not suitable. A suitable vinylpyrrolidone-vinyl acetate copolymer is sold for example by BASF under the tradename Kollidon VA 64 (weight ratio of vinylpyrrolidone to vinyl acetate of 60 to 40). Vinylpyrrolidone-vinyl acetate copolymers are commercially available also from Ashland Inc., USA.

The mean molar mass of soluble polyvinylpyrrolidones is described in the common pharmacopoeias Ph.Eur, USP and JPE by way of the k value. This value is calculated by way of the relative viscosity of aqueous polyvinylpyrrolidone solutions and in the case of polyvinylpyrrolidones from BASF always forms part of the tradename. Thus, PVP K 90 has a mean k value of 90 (81.0-97.2).

The examination methods by viscosimetry are based on the knowledge that a liquid, as a result of an introduced particle, experiences an increase in viscosity that is proportional to the volume of the particle. Since in the case of polymer-homologous series the volume of the macromolecules increases with the molar mass, there must be a correlation between the viscosity increase and molar mass. The relative viscosity increase is referred to generally as specific viscosity. The k value is therefore the specific viscosity of polyvinylpyrrolidone solutions, wherein the solid fraction is 1 or 5%.

The amount of the at least one polymer with at least one acid amide group as a lateral functional group in the TTS is for example at least 10 mg, preferably at least 15 mg, and/or for example no more than 100 mg, preferably no more than 60 mg.

The weight ratio of nicotine to the at least one polymer with at least one acid amide group as a lateral functional group in the TTS is preferably 10:1 to 1:2, especially preferably 5:1 to 1:1, even more preferably 3:1 to 1:1.

By way of the addition of polymer with at least one acid amide group as a lateral functional group, the nicotine contained in the TTS surprisingly can be stabilised such that it does not discolour, or discolours significantly more slowly. Besides this stabilising function, the polymer is also used to set a suitable viscosity of the active-substance-containing composition which is necessary in the case of the preferred production of the TTS for individual dosing.

The above-mentioned commercial products Kollidon (polyvinylpyrrolidone) or Kollidon VA 64 (vinylpyrrolidone-vinyl acetate copolymer) are monographed as pharmaceutical excipients in the common pharmacopoeias Ph.Eur., USP and JPE; see also for example Bühler, Volker, Kollidon® Polyvinylpyrrolidone excipients for the pharmaceutical industry BASF SE 9$^{th}$ edition, March 2008. Both polymer types form addition compounds with protonic substances or acids via hydrogen bridge bonds, however their use for the stabilisation of aprotic-polar oxidation-sensitive substances was not previously known, and therefore their effect for the stabilisation of nicotine is all the more surprising and constitutes an innovation in the pharmaceuticals sector.

Astonishingly, the use of the polymers with at least one acid amide group as a lateral functional group results in an avoidance or slowing of the discolouration of nicotine over time, such that it is possible to use a light-permeable layer or film as back layer without unsightly discolorations being visible.

The TTS comprises a back layer that is impermeable to nicotine. The back layer of a TTS must be impermeable to the active substance contained in the TTS in order to prevent an undesirable leakage of the active substance from the side of the TTS facing away from the skin.

The back layer of the TTS is preferably light-permeable, especially transparent. In an alternative embodiment the back layer can be matt, so that in the TTS the outwardly pointing surface of the back layer is a matt surface.

Layers or films made of plastic, for example polyethylene terephthalate (PET), are most expedient for the back layer. The advantage of these plastic layers or plastic films lies in the fact that they can be produced economically and are impermeable to practically all pharmaceutical active substances. The back layer impermeable to nicotine is preferably a plastic film, especially a transparent plastic film.

Polyesters are suitable as plastics for the active-substance-impermeable back layer, especially for the active-substance-impermeable transparent back layer, especially polyesters that are characterised by particular strength, for example polyethylene terephthalate and polybutylene terephthalate, however other skin-compatible plastics, such as acrylonitrile-methyl acrylate copolymers, for example Barex® films from arbo plastic AG, Switzerland, are also suitable in addition. Composite laminates formed from two or more plastic films can also be used for the back layer.

A film formed from polyethylene terephthalate (PET), especially a transparent film formed from PET, is especially preferably used for the back layer. A large number of different types of suitable PET films are commercially available from Mitsubishi Polyester Film GmbH under the tradename Hostaphan®.

Layers comprising metallic aluminium are often used in the prior art as back layer, especially in the form of composite laminates of aluminium foil and plastic films. However, this is not preferred in accordance with the invention, i.e. preferably no metallic aluminium, for example in the form of an aluminium foil, is provided in the back layer. The back layer is also preferably free or substantially free from colour pigments and dyes.

The back layer is preferably colourless, especially transparent and colourless. The back layer is especially preferably clear or see-through. Suitable transparent films or see-through films are commercially available.

The TTS also comprises a detachable protective layer. Such detachable protective layers are commercially available. The detachable protective layer is likewise impermeable to nicotine.

In principle, the same materials as are used for the back layer can be used for the detachable protective layer, assuming they are provided with a detachable suitable surface treatment, for example a siliconisation. However, other detachable protective layers can also be used, for example paper or Cellophan® (cellulose hydrate) treated with polytetrafluoroethylene.

The layers and fixing device discussed hereinafter are arranged in the TTS between the back layer impermeable to nicotine and the detachable protective layer.

In order to secure a transdermal therapeutic system to the skin and to ensure the controlled administration of the active substance, the TTS is provided especially with a self-adhesive layer. This self-adhesive layer can be identical for example to the matrix layer described hereinafter or the skin-side active-substance-containing layer, but also additionally can be provided if the active-substance-containing layer or an optionally provided membrane or the matrix layer is not self-adhesive.

The transdermal therapeutic system according to the invention therefore comprises especially a layer or a fixing device which is self-adhesive and is arranged on the surface of the detachable protective layer facing the back layer impermeable to nicotine, wherein the self-adhesive layer or fixing device can be, for example, the active-substance-containing layer or a self-adhesive layer or fixing device different therefrom. This self-adhesive layer or fixing device different from the active-substance-containing layer can be, for example, the matrix layer explained further below or an additional self-adhesive layer or fixing device. The particular type of TTS determines which self-adhesive layer or fixing device is arranged on the surface of the detachable protective layer facing the back layer, as will be explained later. Other layers can also be self-adhesive as appropriate.

The detachable protective layer is detached at the time of use, and the TTS exposed by the detachable protective layer is then adhered to the skin at the desired location by means of the above-described layer or fixing device, which is self-adhesive.

Regardless of whether the layer or fixing device, which is self-adhesive, is the active-substance-containing layer, the matrix layer or an additional self-adhesive layer or fixing device, the layer or fixing device that is self-adhesive comprises especially a pressure-sensitive adhesive. The pressure-sensitive adhesive is based on at least one polymer. Such polymers are well known in the art. Suitable examples of polymers for the pressure-sensitive adhesive will be provided hereinafter.

The pressure-sensitive adhesive preferably comprises at least one polymer selected from poly(meth)acrylates, polyisobutylene, polyvinyl acetate, ethylene-vinyl acetate copolymer, natural and/or synthetic rubbers, styrene-diene copolymers such as styrene-butadiene block copolymers, polyesters, polychloroprenes, polyvinyl ethers, polyurethanes, silicone polymers, which are also referred to as polysiloxanes, or a hot-melt adhesive.

Examples of natural and/or synthetic rubbers are acrylonitrile butadiene rubber, butyl rubber or neoprene rubber. Poly(meth)acrylates are polymers of one or more monomers selected from acrylic esters and/or methacrylic esters and/or acrylic acid and/or methacrylic acid and optionally additional comonomers, such as vinyl acetate, wherein at least one acrylic ester or methacrylic ester is preferably contained. The acrylates of one or more acrylic esters and optionally acrylic acid and/or one additional comonomer, such as vinyl acetate, are preferred. The silicone polymer can be a silicone rubber, for example.

The polymers for the pressure-sensitive adhesive are especially polymers with a glass transition temperature (Tg)<0° C., which are suitable as matrix-forming polymers. The at least one polymer for the pressure-sensitive adhesive is preferably light-permeable or transparent.

Besides the above-mentioned polymers, the pressure-sensitive adhesive can also optionally contain further constituents, for example at least one resin and/or plasticiser. One example is constituted by triglycerides of fatty acids.

The additional adhesive layer or fixing device can be configured as a layer. Alternatively, it can be a self-adhesive fixing device, which is arranged between the detachable protective layer and the layer thereabove. The fixing device can be formed for example by pressure-sensitive adhesive portions, for example a peripheral adhesive edge or also adhesive spots, embedded in the layer thereabove.

The TTS can optionally additionally comprise a membrane. Whereas the active-substance-containing layer or matrix layer comprises especially one or more polymers with a Tg<0° C., in which substances can be dissolved, an optional membrane is formed from one or more polymers with a Tg>0° C. Substances are not dissolved by a membrane formed from such polymers, and therefore the membrane must have holes or pores, through which the substance can diffuse. The release of the active substance from a matrix layer and a membrane follow different principles of kinetics. The membrane, if provided, can be arranged for example between active-substance-containing layer or matrix layer and a fixing device.

The TTS according to the invention can be used for different types of TTS which are known in the art. Different embodiments are provided depending on the type and will be explained hereinafter.

In a first embodiment the active-substance-containing layer, besides nicotine and the at least one polymer with at least one acid amide group as a lateral functional group, can additionally comprise at least one polymer for forming a matrix, preferably an adhesive matrix. However, the matrix may also not be self-adhesive. The at least one polymer for forming a matrix can be a polymer for the pressure-sensitive adhesive defined above. Reference is made to the examples given there. Other suitable polymers for the at least one polymer for forming a matrix are in principle polymers with a glass transition temperature Tg<0° C., because the polymer then acts as a matrix when it is in the rubber state.

In the first embodiment the active-substance-containing layer can be self-adhesive. It then preferably comprises a pressure-sensitive adhesive containing the at least one polymer for the pressure-sensitive adhesive as defined above. In this case, the TTS can comprise or can be formed from the back layer, the self-adhesive active-substance-containing layer, and the detachable protective layer. A TTS of this kind is also referred to as a monolithic matrix TTS.

In the first embodiment, besides the active-substance-containing layer, which comprises the at least one polymer for forming a matrix, an additional self-adhesive layer or fixing device can also be comprised, which is arranged between the active-substance-containing layer and the detachable protective layer. In this variant the active-substance-containing layer does not necessarily need to be self-adhesive. The additional self-adhesive layer or fixing device has been defined above and then preferably comprises a pressure-sensitive adhesive containing the at least one polymer for the pressure-sensitive adhesive as described above. A TTS of this kind is also referred to as a multi-layer matrix TTS.

In the first embodiment the joint fraction of nicotine and the at least one polymer with at least one acid amide group as a lateral functional group in the active-substance-containing layer is, for example, 1 to 20% by weight, preferably 5 to 15% by weight, in relation to the weight of the active-substance-containing layer.

In a second and preferred embodiment the TTS additionally comprises a matrix layer for controlling the release of the active substance or of the nicotine and optionally an additional self-adhesive layer or fixing device, which is arranged between the matrix layer and the detachable protective layer. The matrix layer can be self-adhesive. In this case the additional self-adhesive layer or fixing device is not necessary. In the second embodiment it is preferred that the TTS comprises the self-adhesive layer or fixing device between the detachable protective layer and the matrix layer. In this case the matrix layer does not necessarily need to be self-adhesive.

The matrix layer and the self-adhesive layer or fixing device of the TTS according to the invention can consist of the same material or can consist of different materials.

The matrix layer for controlling the release of the active substance preferably comprises at least one polymer for forming a matrix, preferably an adhesive matrix. The at least one polymer for forming a matrix can be a polymer for the adhesive explained above. Reference is made to the examples given there. Matrix-forming polymers are also self-adhesive.

The matrix layer for controlling the release of the active substance is preferably free from active substance in the original state.

The additional self-adhesive layer or fixing device provided optionally and preferably in the second embodiment has already been defined above and preferably comprises a pressure-sensitive adhesive containing the least one polymer for the pressure-sensitive adhesive as described above. Reference is made to the examples given there.

The matrix layer and/or the additional self-adhesive layer or fixing device, if provided, can optionally comprise a material selected from cationic copolymers based on dimethylaminoethyl methacrylate and neutral methacrylic esters, and neutral copolymers based on butyl methacrylate and methyl methacrylates. An example is Eudragit® E 100 (cationic copolymer based on dimethylaminoethyl methacrylate, butyl methacrylate and methyl methacrylate in a ratio of 2:1:1).

If the matrix layer is self-adhesive, it preferably comprises a pressure-sensitive adhesive containing the at least one polymer for the pressure-sensitive adhesive as described above. The matrix layer can also be formed in a number of layers, for example two layers, wherein the individual layers for example contain different types of ingredients or different concentrations of the ingredients, for example so as to form a gradient.

In the second embodiment the active-substance-containing layer can be embedded in the matrix layer for controlling the release of the nicotine and/or can be arranged on the surface of the matrix layer facing the back layer. It is preferred here that the active-substance-containing layer is embedded in the back layer or is arranged on the surface of the matrix layer only over part of the area, for example in a central region of the matrix layer. It is also possible that the active-substance-containing layer is not embedded in the back layer or arranged on the surface of the matrix layer in the form of a continuous layer, but instead in the form of two or more partial layers.

As already mentioned above, it is preferred that in this embodiment an additional self-adhesive layer or fixing device as defined above is provided between the matrix layer and the detachable protective layer.

In the second embodiment the active-substance-containing layer, besides nicotine and the at least one polymer with at least one acid amide group as a lateral functional group, preferably comprises only a small proportion of further constituents, or no further constituents.

In the second embodiment the joint fraction of nicotine and the at least one polymer with at least one acid amide group as a lateral functional group in the active-substance-containing layer is accordingly, for example, 1 to 100% by weight, preferably 5 to 100% by weight, more preferably 5 to 75% by weight, in relation to the weight of the active-substance-containing layer. In a preferred embodiment the joint fraction of nicotine and the at least one polymer with at least one acid amide group as a lateral functional group in the active-substance-containing layer is 60 to 100% by weight, preferably 80 to 100% by weight, more preferably 90 to 100% by weight, in relation to the weight of the active-substance-containing layer.

The matrix layer controls the release of the nicotine. In the original state the matrix layer is preferably free from active substance. The nicotine contained in an active-substance-containing layer diffuses or flows into the matrix layer over time, possibly until a saturation concentration is reached. When the TTS is used, the nicotine concentration in the matrix layer reduces as a result of being absorbed by the skin. Further nicotine can then diffuse into the matrix layer from the active-substance-containing layer as appropriate. The diffusion of nicotine into the matrix layer starts directly after application of the active-substance-containing layer to the matrix layer. It therefore goes without saying that the composition of the active-substance-containing layer can change over time. The details provided above in relation to the active-substance-containing layer therefore relate especially to the active-substance-containing composition used in order to form the active-substance-containing layer, but generally apply also to the active-substance-containing layer following production of the TTS.

In the second embodiment the active-substance-containing layer is preferably a semi-solid layer. The active-substance-containing layer is preferably obtainable by applying an active-substance-containing composition which has a Brookfield viscosity in the range of from 10 to 100 dPa·s, especially preferably in a range of from 15 to 30 dPa·s, determined at room temperature (20° C.).

The transdermal therapeutic system may optionally contain at least one acid, for example an organic acid, such as tartaric acid and salicylic acid, or an inorganic acid, such as hydrochloric acid, however this is not preferred. The TTS, especially the active-substance-containing layer, is preferably substantially free from acid. The proportion of acid in the TTS without back layer and detachable protective film for example should be no more than 2% by weight, preferably no more than 0.5% by weight, more preferably no more than 0.02% by weight, in relation to the weight of the transdermal therapeutic system without back layer and detachable protective film. This is true especially for the proportion of acid in the TTS without back layer and detachable protective layer. The TTS is especially preferably free from acid because nicotine salts do not diffuse through the skin.

The transdermal therapeutic system may optionally contain one or more antioxidants in one or more of the above-mentioned layers. However, the TTS is preferably free from antioxidants, at least in the layers that are different from the detachable protective layer and the back layer.

Typical thicknesses for TTS according to the invention are: total thickness of approximately 123 μm to 5550 μm, preferably 285 μm to 1550 μm; thickness of the back layer impermeable to nicotine of from 8 to 50 μm, preferably 15 to 25 μm.

Due to the stabilisation according to the invention of the nicotine by the acid-amide-containing polymer, there is no discolouration or only a very slowed discolouration. Transparent TTS can therefore be provided in accordance with the invention. In a especially preferred embodiment a transparent back layer is therefore used, wherein the further layers of the TTS are also light-permeable, apart from the detachable protective layer, which does not necessarily need to be light-permeable. In this application the TTS is almost invisible in relation to the skin to which it is adhered, since the natural skin colour of the user is visible through the TTS.

The invention also relates to a method for producing a transdermal therapeutic system according to the invention as described above, wherein the method comprises the following steps providing a first carrier layer or producing a starting laminate comprising a first carrier layer, applying a flowable active-substance-containing composition, comprising nicotine as active substance, wherein the nicotine is in the form of a free base, and at least one polymer with at least one acid amide group as a lateral functional group, to the first carrier layer or the starting laminate, and laminating the rest of the layers of the transdermal therapeutic system, comprising a second carrier layer, onto the first carrier layer provided with the active-substance-containing composition or the starting laminate provided with the active-substance-containing composition, wherein the transdermal therapeutic systems can be separated by being cut and/or punched from the product or laminate created up to that point, before or after the application of the active-substance-containing composition, and the first carrier layer forms the detachable protective layer, which preferably is impermeable to nicotine, and the second carrier layer forms the back layer impermeable to nicotine, or vice versa.

The joint fraction of nicotine and the at least one polymer with at least one acid amide group as a lateral functional group in the flowable active-substance-containing composition is, for example, 1 to 100% by weight, preferably 5 to 100% by weight. In a further preferred embodiment the joint action of nicotine and the at least one polymer with at least one acid amide group as a lateral functional group in the flowable active-substance-containing composition is 60 to 100% by weight, preferably 80 to 100% by weight, more preferably 90 to 100% by weight, in relation to the weight of the flowable active-substance-containing composition.

The first carrier layer is preferably the detachable protective layer, which preferably is impermeable to nicotine. The second carrier layer is preferably the back layer, which is impermeable to nicotine and preferably is transparent.

The lamination of the rest of the layers of the transdermal therapeutic system, comprising a second carrier layer, can be performed here by applying the rest of the layers individually in succession or preferably by laminating the rest of the layers together as a whole. Of course, the lamination can also be performed by a combination of lamination of one or more of the rest of the layers individually and/or of two or more of the rest of the layers together.

The separation by cutting and/or punching is preferably performed following the application of the active-substance-containing composition, for example once all layers of the TTS have been connected to one another. However, it is also possible to separate the TTS from the composite laminate formed up to that point, after application of the active-substance-containing preparation, but prior to the application of the back layer, and to only then cover the TTS with a back layer.

In a preferred embodiment the method according to the invention comprises the following steps producing the starting laminate comprising the first carrier layer and a matrix layer or part of a matrix layer, wherein a self-adhesive layer or fixing device is arranged optionally between the first carrier layer and the matrix layer, applying the flowable active-substance-containing composition to the matrix layer or the part of the matrix layer, and laminating the rest of the layers of the transdermal therapeutic system, comprising the second carrier layer, onto the matrix layer provided with the active-substance-containing composition, wherein, if the starting laminate comprises only a part of the matrix layer, the rest of the matrix layer is applied as first layer to the partial matrix layer provided with the active substance composition.

The part of the matrix layer refers here to a part in the thickness direction. For example, approximately half or two thirds or any other part of the total thickness of the matrix layer can be applied first, and the rest of the thickness of the matrix layer can be applied following application of the active-substance-containing composition.

The flowable active-substance-containing composition is applied preferably by way of a printing method in which individually dosed portions of the flowable, active-substance-containing composition are applied to the starting laminate or the matrix layer or the part of the matrix layer. Especially, the individually dosed portions are applied over part of the area.

The above-mentioned printing method can be a pad printing method. Such a method is known for example from patent document U.S. Pat. No. 5,110,599, to which reference is made in full.

The above-mentioned printing method may additionally be a method in which the active-substance-containing preparation is transferred, by a distribution plate of an application device provided with at least one aperture, to the matrix layer intended to receive the active substance. A method of this kind is known from patent document U.S. Pat. No. 6,187,322, to which reference is made in full.

The active substance nicotine can be directly applied by means of the two above-mentioned printing methods. However, in accordance with the invention, the active substance is used in the form of a solution, which has the desired viscosity as a result of the addition of the at least one polymer with at least one acid amide group as a lateral functional group. The Brookfield viscosity of the active-substance-containing composition to be used as printing medium lies preferably in the range of from 10 to 100 dPa·s, especially preferably in a range of from 15 to 30 dPa·s, measured on a sample of which the temperature has been controlled to 20° C.

In order to determine the Brookfield viscosity a rotational viscometer is used, for example the VT 500 from the company Haake, under the following conditions: system number 25, speed 8, rotary body ISO 3 d6.

The separation is preferably performed such that the cutting and/or punching are/is performed only outside the area onto which the nicotine solution was printed or partially printed. In this way, production-induced active substance losses can be largely avoided. In this way, the active-substance-containing layer is preferably located in the central region of the formed TTS, whereas the edge region of the TTS does not comprise any active-substance-containing layer.

The method for producing the TTS according to the invention is characterised in a especially preferred embodiment in that a laminate formed from an active-substance-impermeable carrier layer (for the detachable protective layer), a self-adhesive fixing layer, and a matrix layer or part of the matrix layer is produced, individually dosed portions of the flowable, active-substance-containing preparation are applied to this matrix layer, especially over part of the area, by means of a printing method, a further matrix layer or the rest of the matrix layer is laminated thereon optionally, and the resultant laminate is lastly provided with an active-substance-impermeable back layer, wherein the transdermal therapeutic systems can be separated by cutting and/or punching from the composite laminate produced up to that point, prior to or after the application of the active-substance-containing preparation.

The separation is performed especially such that the cutting and/or punching are/is performed only outside the area onto which the nicotine solution was printed.

The invention also relates to the use of a polymer with at least one acid amide group as a lateral functional group for stabilising nicotine in a nicotine-containing transdermal therapeutic system, especially in the TTS according to the invention.

As a result of the stabilisation of the nicotine, especially the discolouration of nicotine in the TTS that would occur during storage of a TTS without this stabilisation is slowed or avoided. A slowing or avoidance of the discolouration of nicotine shall be understood to mean especially that the discolouration from colourless to light yellow does not exceed the colour Pantone 1215, especially preferably Pantone 2015 C, for example after storage for 3 months in the dark in air at 25° C., more preferably at 40° C., and especially preferably at 60° C.

The invention also relates to a method for stabilising nicotine in a nicotine-containing transdermal therapeutic system, comprising the charging of the transdermal therapeutic system with a polymer with at least one acid amide group as a lateral functional group during the production.

The invention also relates to the use of a TTS according to the invention for a therapeutic system on the skin, wherein the active substance is released transdermally in a prophylactically or therapeutically effective amount, preferably over a period of time of at least 24 hours.

The TTS according to the invention demonstrates a very good active substance yield. The residual nicotine content in the TTS after 24 hours of use on the skin may be at most 60% (in an environment at room temperature).

Figure 2:
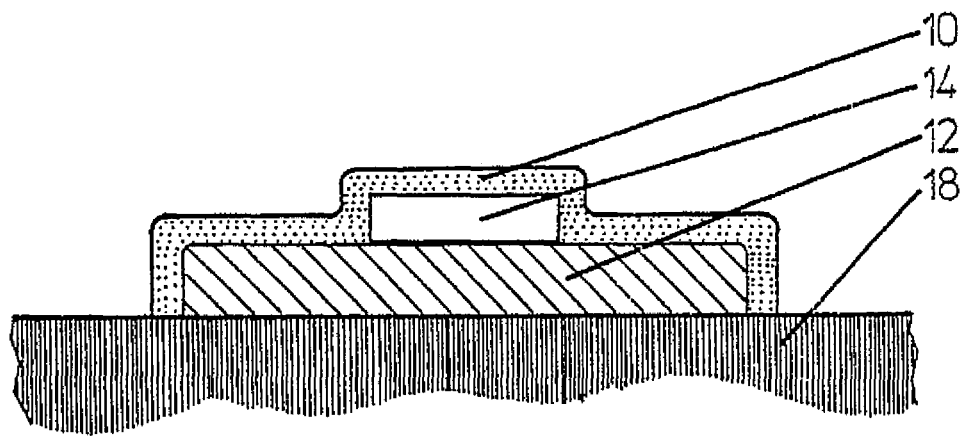

The invention will be explained hereinafter with reference to a practical example and the accompanying drawings, which schematically shows the structure of an example of a TTS according to the invention, without the invention being limited to this. In the drawings:

FIG. 1 shows a section through a preferred embodiment of a TTS according to the invention; and FIG. 2 shows a section through a further preferred embodiment of a therapeutic system in which the active-substance-containing layer is located between the back layer and matrix layer in the form of a reservoir for nicotine. The TTS is shown adhered to the skin following removal of the detachable protective layer.

The active-substance-containing layer from FIG. 1 and FIG. 2 comprises nicotine and the polymer with at least one acid amide group.

FIG. 1 schematically shows a section through a therapeutic system according to the invention which is secured to the skin 18 by a self-adhesive fixing layer 16. The matrix layer 12, which is preferably free from active substance at the time of production (the saturation with active substance occurs during storage) is located on the self-adhesive layer 16. An active-substance-containing layer 14 is embedded in the matrix layer, and nicotine dissolves or diffuses out from the active-substance-containing layer and is delivered to the skin through the self-adhesive layer 16. The therapeutic system is terminated outwardly by a transparent back layer 10, which is impermeable to the active substance nicotine and preferably also to moisture and at the same time performs a supporting function for the system.

In FIG. 2 the active-substance-containing layer 14 is located between the back layer 10 and the matrix layer 12. The matrix layer 12 is self-adhesive and is secured to the skin 18. Alternatively, a self-adhesive layer (corresponding to the layer 16 from FIG. 1) or a self-adhesive device could be arranged between the matrix layer 12 and the skin 18 (not shown). In this case the matrix layer is not necessarily self-adhesive.

EXAMPLES

Reference Examples

Since polyisobutylenes contain terminal double bonds and therefore have to be stabilised by the antioxidant butyl hydroxytoluene, it was examined whether the avoidance of nicotine discolouration can be achieved by antioxidants. Pharmaceutically acceptable antioxidants were therefore added to nicotine in graded-concentrations in 2 test series to form solutions of Eudragit E 100 (cationic copolymer based on dimethylaminoethyl methacrylate, butyl methacrylate and methyl methacrylate in a ratio of 2:1:1). These solutions were stored in the dark for 4 weeks at 60° C. or 80° C.

Butyl hydroxytoluene (BHT), ascorbyl palmitate and tocopherol were tested as antioxidants. The compositions of the tested samples are summarised in Table 1.

TABLE 1

Nicotine Eudragit E 100 solutions, which were stored at 60° C. and 80° C.

| Substance | Reference [%] w/w | Reference* [%] w/w | Nic 0001 [%] w/w | Nic 0002 [%] w/w | Nic 0003 [%] w/w | Nic 0004 [%] w/w | Nic 0005 [%] w/w | Nic 0006 [%] w/w | Nic 0007 [%] w/w | Nic 0008 [%] w/w | Nic 0009 [%] w/w | Nic 0010 [%] w/w |
|---|---|---|---|---|---|---|---|---|---|---|---|---|
| Nicotine | 58.30 | 58.30 | 99.95 | 99.85 | 99.50 | 99.00 | 99.95 | 99.85 | 99.50 | 99.95 | 99.85 | 99.50 |
| Eudragit E 100 | 41.70 | 41.70 | | | | | | | | | | |
| Butyl hydroxytoluene(BHT) | / | / | 0.05 | 0.15 | 0.50 | 1.00 | / | / | / | / | / | / |
| Ascorbyl palmitate | / | / | / | / | / | / | 0.05 | 0.15 | 0.50 | / | / | / |

TABLE 1-continued

Nicotine Eudragit E 100 solutions, which were stored at 60° C. and 80° C.

| Substance | Reference [%] w/w | Reference* [%] w/w | Nic 0001 [%] w/w | Nic 0002 [%] w/w | Nic 0003 [%] w/w | Nic 0004 [%] w/w | Nic 0005 [%] w/w | Nic 0006 [%] w/w | Nic 0007 [%] w/w | Nic 0008 [%] w/w | Nic 0009 [%] w/w | Nic 0010 [%] w/w |
|---|---|---|---|---|---|---|---|---|---|---|---|---|
| Tocopherol (VitE) | / | / | / | / | / | / | / | / | / | 0.05 | 0.15 | 0.50 |

*N₂ flooded

The samples were examined visually after storage, and the relevant Pantone Colour Code for the colour of the sample was determined. The Pantone Colour Code is an internationally used colour system developed by the company Pantone LLC, USA. As a result it is possible to determine that the antioxidants were unable to suppress the discolouration of the nicotine. For example, the nicotine/Eudragit solution with 0.05, 0.15 and 0.5% ascorbyl palmitate (AP, Nic 0005-Nic 0007) at 80° C. demonstrated a significant brown colouration after 4 weeks:

| Nic 0005 (+0.05% AP) | Pantone Colour Code: 7580C |
| Nic 0006 (+0.15% AP) | Pantone Colour Code: 7675C |
| Nic 0007 (+0.5% AP) | Pantone Colour Code: 7589C |

In order to check which decomposition products of nicotine cause the brown colour, sample Nic 0007 was analysed. The results are summarised in Table 2.

TABLE 2

Comparison of degradation products (mean values from n = 3) [%]

| Sample | Cotinine | Myosmine | Unknown |
|---|---|---|---|
| Reference | 0.06 | 0.13 | <0.05 |
| Nic0001 | 0.05 | 0.15 | <0.05 |
| Nic0007 | 0.03 | 0.09 | <0.05 |

It can be seen that ascorbyl palmitate does not prevent the brown colouration of nicotine, but does prevent its decomposition.

Irganox was therefore also examined in comparison to BHT with regard to a nicotine-stabilising effect, wherein lower temperatures were used for the storage. The compositions and mixing ratios of the samples are shown in Table 3.

As a result it can be determined that in this test series as well it was not possible to suppress the discolouration of nicotine. For example, nicotine Eudragit E 100 with 0.03% Irganox demonstrated the following discolouration after 3 months of storage:

| 997Nic0005-1 stored at 25° C. | Pantone Colour Code: 120C |
| 997Nic0005-3 stored at 40° C. | Pantone Colour Code: 7549C |
| 997Nic0005-5 stored at 60° C. | Pantone Colour Code: 7618C |

Since, clearly, the discolouration of the nicotine cannot be suppressed by antioxidants, other ways of achieving this were sought. Neutral polymers were dissolved in nicotine in order to achieve high viscosity for the printing method.

The polymers named below were tested mixed with nicotine. The mixtures were stored at 25° C., 40° C. and 60° C. for a period of 3 months in the dark in air. The compositions and mixing ratios of the samples are shown in Table 4.

Used polymers for mixture with nicotine:

| Plastoid B | methyl methacrylate-butyl methacrylate copolymer (1:1) from Evonik |
| Eudragit L100-55 | methacrylic acid-ethyl acrylate copolymer (1:1) from Evonik Industries |
| 12500 cST Silicone oil | Silicone oil |
| Povidone K-90 | polyvinylpyrrolidone, Kollidon ® 90 F from BASF |
| Povidone VA 64 | vinyipyrrolidone-vinyl acetate copolymer, Kollidon ® VA 6:4 from BASF |

TABLE 3

Nicotine Eudragit E 100 solutions, which were stored at 25° C., 40 ° C. and 60° C.

| Substance | Reference [%] w/w | Reference Nicotine [%] w/w | Mc + BHT [%] w/w | Nic + Irgan. [%] w/w | 997Nic 0001 [%] w/w | 997Nic 0002 [%] w/w | 997Nic 0003 [%] w/w | 997Nic 0004 [%] w/w | 997Nic 0005 [%] w/w | 997Nic 0006 [%] w/w | 997Nic0 007 [%] w/w | 997Nic0 008 [%] w/w |
|---|---|---|---|---|---|---|---|---|---|---|---|---|
| Nicotine Eudragit E 100 | 58.30 41.70 | 100.0 / | 99.0 / | 99.0 / | 99.995 ᵃ | 99.99 ᵃ | 99.97 ᵃ | 99.91 ᵃ | 99.97 ᵃ | 99.91 ᵃ | 99.5 ᵃ | 99.0 ᵃ |
| Butyl hydroxytoluene (BHT) | / | / | 1.0 | / | 0.005 | 0.01 | 0.03 | 0.09 | / | / | / | / |
| Irganox ® 1010 | / | / | / | 1.0 | / | / | / | / | 0.03 | 0.09 | 0.5 | 1.0 |

ᵃ Ratio of nicotine (58.30 w/w %) and Eudragit E 100 (41.70 w/w %)

TABLE 4

Nicotine polymer solutions, which were stored at 25° C., 40° C. and 60° C.

| Substance | Plasbid B [%] w/w | Eudragit L100-55** [%] w/w | Silicone oil 12500 ca** [%] w/w | Povidone K-90 [%]w/w | 997Nic 0009 [%] w/w | 997Nic 0010** [%] w/w | 997Nic 0011** [%] w/w | 997Nic 0013 [%] w/w | 997 Nic0014* [%] w/w | 536 Nic0002 [%] w/w |
|---|---|---|---|---|---|---|---|---|---|---|
| Nicotine | / | / | / | / | 58.30 | 58.30 | 58.30 | 90.0 | 100.0 | 67.0 |
| Plastoid B | 100.0 | / | / | / | 41.70 | / | / | / | / | / |
| Eudragit L100-55 | / | 100.0 | / | / | / | 41.70 | / | / | / | / |
| Silicone oil 12500 cST | / | / | 100.0 | / | / | / | 41.70 | / | / | / |
| Povidone K-90 | / | / | / | 100.0 | / | / | / | 10.0 | / | / |
| Povidone VA 64 | / | / | / | / | / | / | / | / | / | 33.0 |

*pure nicotine
**Eudragit L100-55 and silicone oil 12500 cST are not compatible with nicotine Eudragit L100-55 and silicone oil 12500 cST are not compatible with nicotine. Plastoid B demonstrates phase separation.

In the case of nicotine with 10% PVP (Kollidon K-90 F) the sample that was stored at 60° C. was only slightly discoloured after 3 months of storage. The samples stored at 25° C. and 40° C. were discoloured even less and were practically unchanged. The colours are stated below in accordance with Pantone Colour Codes for the samples with PVP:

997Nic0013-1 initial Pantone Colour Code: 7401C
997Nic0013-1 stored at 25° C. Pantone Colour Code: 2015C
997Nic0013-3 stored at 40° C. Pantone Colour Code: 2015C
997Nic0013-5 stored at 60° C. Pantone Colour Code: 7549C The nicotine Eudragit E 100 solution, immediately after production, has the colour Pantone 1205 and discolours within 3 months of storage at 25° C. or 40° C. to Pantone 1215 C, whereas the colour brown was achieved at 60° C.

Nicotine solutions with PVP VA 64 similarly to the PVP solutions start at 7401C and, regardless of the storage temperature 25° C., 40° C. or 60° C., reach only the colour Pantone 1215 C.

A nicotine TTS was therefore produced in which Eudragit E 100 was not used to increase the viscosity of the nicotine base, but instead vinylpyrrolidone-vinyl acetate copolymer (Kollidon® VA 6:4 (weight ratio of vinylpyrrolidone to vinyl acetate of 60 to 40, from BASF)).

Example

A pressure-sensitive adhesive compound HS was firstly produced by homogenising a) 933 g of a commercial product (®Duro-Tak 387-2516 from the company Henkel, Düsseldorf, Germany—this is a 40% solution of self-crosslinking acrylate polymer based on 2-ethylhexyl acrylate, vinyl acetate, acrylic acid and titanium chelate ester in a solvent mixture of ethyl acetate, ethanol, heptane and methanol) with b) 8 g of a triglyceride of fractionated coconut fatty acids (C8-C10; ®Miglyol 812 from the company Evonik Witten, Germany).

In addition 6210 g®Duro-Tak 387-2516, 553 g ethyl acetate and 311 g ethanol were mixed and homogenised with 66 g of the aforementioned triglyceride and 626 g of an acrylic resin formed from dimethylaminoethyl methacrylate and neutral methacrylic esters (®Eudragit E 100 from the company Röhm-Pharma, Darmstadt, Germany) (adhesive compound MS).

In addition 33 g vinylpyrrolidone-vinyl acetate copolymer (Kollidon® VA 64) were introduced into 66 g nicotine and dissolved therein. This resulted in the active substance preparation.

The pressure-sensitive adhesive compound HS was applied to an adhesive protective layer (A) such that, after evaporation of the solvent, a pressure-sensitive adhesive layer with a weight per unit area of 40 g/m$^2$ was formed.

The adhesive compound MS was applied to another adhesive protective layer (B) such that, after evaporation of the solvent, a film with a weight per unit area of 220 g/m$^2$ was produced. This film was laminated onto the pressure-sensitive adhesive layer applied to the protective layer (A). This resulted in the bottom web.

In a further coating step the adhesive compound MS was applied to a further adhesive protective layer (C) such that, after evaporation of the solvent, a film with a weight per unit area of 110 g/m$^2$ was produced, onto which the transparent back layer impermeable to the active substance was laminated. The top web was thus formed.

Following the removal of the adhesive protective layer (B) from the bottom web, the active substance preparation was printed by means of an egg-shaped silicone-foamed rubber pad with a Shore hardness of 6 onto the adhesive web. The amount of active substance preparation was such that each TTS later contained 30 mg of nicotinic vinylpyrrolidone-vinyl acetate copolymer.

The top web was laminated onto the bottom web (provided with doped active substance preparation) following removal of the adhesive protective layer (C), and TTS were punched out.

A TTS according to the schematic structure of FIG. 1 was obtained.

The invention claimed is:
1. A transdermal therapeutic system (TTS), comprising
a) a back layer, impermeable to nicotine,
b) an active-substance-containing layer, comprising nicotine as active substance, wherein the nicotine is in the form of a free base and a vinylpyrrolidone-vinyl acetate copolymer, and wherein the weight ratio of nicotine to vinylpyrrolidone-vinyl acetate copolymer in the active substance-containing layer is 5:1 to 1:1, wherein the residual nicotine content at 24 hours of use on skin is at most 60% at room temperature; and c) a detachable protective layer,
    wherein a joint fraction comprising nicotine and the vinylpyrrolidone-vinyl acetate copolymer in the active-substance-containing layer is 90 to 100% by weight, in relation to the weight of the active-substance-containing layer, wherein the transdermal therapeutic system contains 10 to 400 mg of nicotine.

2. The transdermal therapeutic system according to claim 1, wherein the vinylpyrrolidone-vinyl acetate copolymer is partially hydrolysed.

3. The transdermal therapeutic system according to claim 1, wherein the transdermal therapeutic system contains 15 to 400 mg of nicotine.

4. The transdermal therapeutic system according to claim 1, wherein the back layer comprises at least one polymer selected from the group of polyesters, polyethylene terephthalate and polybutylene terephthalate.

5. The transdermal therapeutic system according to claim 1, wherein a layer or fixing device, which is self-adhesive, is arranged on the surface of the detachable protective layer, which faces the back layer, wherein the self-adhesive layer or fixing device can be the active-substance-containing layer or an additional self-adhesive layer or fixing device.

6. The transdermal therapeutic system according to claim 5, wherein the self-adhesive layer or fixing device, which is self-adhesive, is the additional self-adhesive layer or fixing device and comprises a pressure-sensitive adhesive comprising a polymer selected from natural or synthetic rubbers, poly(meth)acrylates, polyesters, polychloroprenes, polyisobutenes, polyvinyl ethers, polyurethanes, polyvinyl acetates, ethylene-vinyl acetate copolymers, styrene-diene copolymers, styrene-butadiene block copolymers, and silicones, or a hot-melt adhesive.

7. The transdermal therapeutic system according to claim 1, wherein the transdermal therapeutic system also comprises d) a matrix layer for controlling the release of the active substance, wherein the matrix layer is a self-adhesive layer and/or the transdermal therapeutic system also comprises e) a self-adhesive layer or fixing device which is arranged between the detachable protective layer and the matrix layer.

8. The transdermal therapeutic system according to claim 7 including each of d) and e), wherein the self-adhesive layer or fixing device is located between the detachable protective layer and the matrix layer.

9. The transdermal therapeutic system according to claim 7, wherein the matrix layer and/or the self-adhesive layer or fixing device, if provided, comprise/comprises a material that is selected from the group consisting of cationic copolymers based on dimethylaminoethyl methacrylate and neutral methacrylic esters, and neutral copolymers based on butyl methacrylate and methyl methacrylates.

10. The transdermal therapeutic system according to claim 7, wherein the active-substance-containing layer is embedded in the matrix and/or is arranged on the surface of the matrix layer facing the back layer.

11. The transdermal therapeutic system according to claim 1, wherein the active-substance-containing layer is a self-adhesive layer.

12. The transdermal therapeutic system according to claim 1, wherein the back layer impermeable to nicotine is transparent.

13. The transdermal therapeutic system according to claim 1, wherein a proportion of acid in the transdermal therapeutic system without back layer and detachable protective film is no more than 2% by weight, in relation to the weight of the transdermal therapeutic system without back layer and detachable protective film, wherein the active-substance-containing layer is substantially free from acid.

14. The transdermal therapeutic system according to claim 1 wherein the transdermal therapeutic system is transparent.

15. A transdermal therapeutic system (TTS), comprising:
    a) a transparent back layer impermeable to nicotine comprised of polyester;
    b) an active-substance-containing layer comprising nicotine as active substance, wherein the nicotine is in the form of a free base and a vinylpyrrolidone-vinyl acetate copolymer, and wherein the weight ratio of nicotine to vinylpyrrolidone-vinyl acetate copolymer in the active substance-containing layer is 5:1 to 1:1, wherein the residual nicotine content at 24 hours of use on skin is at most 60% at room temperature;
    c) a matrix layer comprised of a material selected from cationic copolymers based on dimethylaminoethyl methacrylate and neutral methacrylic esters, and neutral copolymers based on butyl methacrylate and methyl methacrylates; and
    d) a detachable protective layer;
    wherein a joint fraction comprising nicotine and the vinylpyrrolidone-vinyl acetate copolymer in the active-substance-containing layer is 90 to 100% by weight in relation to the weight of the active-substance-containing layer, wherein the transdermal therapeutic system contains 10 to 400 mg of nicotine, and wherein said TTS is transparent.

16. The transdermal therapeutic system of claim 15, further comprising an adhesive layer disposed on a surface of the matrix layer opposite the active-substance-containing layer.

17. A method for producing a transdermal therapeutic system according to claim 1, wherein the method comprises the following steps
    providing a first carrier layer or producing a starting laminate comprising a first carrier layer,
    applying a flowable active-substance-containing composition, comprising nicotine as active substance, wherein the nicotine is in the form of a free base, and at least one polymer with at least one acid amide group as a lateral functional group, wherein the polymer with at least one acid amide group as a lateral functional group is a vinylpyrrolidone-vinyl acetate copolymer to the first carrier layer or the starting laminate, and
    laminating the rest of the layers of the transdermal therapeutic system, comprising a second carrier layer, onto the first carrier layer provided with the active-substance-containing composition or the starting laminate provided with the active-substance-containing composition,
wherein the transdermal therapeutic systems can be separated by being cut and/or punched from the product or laminate created up to that point, before or after the application of the active-substance-containing composition, and the first carrier layer forms the detachable protective layer, which is impermeable to nicotine, and the second carrier layer forms the back layer impermeable to nicotine, or vice versa.

18. The method according to claim 17, wherein the method comprises the following steps
    producing the starting laminate comprising the first carrier layer and a matrix layer or part of a matrix layer, wherein a self-adhesive layer or fixing device is arranged optionally between the first carrier layer and the matrix layer, applying the flowable active-substance-containing composition to the matrix layer or the part of the matrix layer, and laminating the rest of the layers of the transdermal therapeutic system, comprising the second carrier layer, onto the matrix layer provided with the active-substance-containing composition, wherein, if the starting laminate comprises only a part of the matrix layer, the rest of the matrix layer is applied as first layer to the partial matrix layer provided with the active substance composition.

19. The method according to claim 17, wherein, in order to apply the flowable active-substance-containing composition by means of a printing method, individually dosed portions of the flowable, active-substance-containing composition are applied to the first carrier layer or the matrix layer or the part of the matrix layer.

20. The method according to claim 19, characterised in that the printing method is a pad printing method, or in that the printing method is a method in which the flowable active-substance-containing composition is transferred to the first carrier layer or the matrix layer or the part of the matrix layer by a distributor plate of an application device provided with at least one aperture.

* * * * *